US00PP30124P3

(12) United States Plant Patent
Goffreda

(10) Patent No.: US PP30,124 P3
(45) Date of Patent: Jan. 22, 2019

(54) NECTARINE TREE NAMED 'NJF20'

(50) Latin Name: ***Prunus persica* L.**
Varietal Denomination: NJF20

(71) Applicant: RUTGERS, THE STATE UNIVERSITY OF NEW JERSEY, New Brunswick, NJ (US)

(72) Inventor: Joseph C. Goffreda, Millstone Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 18 days.

(21) Appl. No.: 15/530,785

(22) Filed: Feb. 28, 2017

(65) Prior Publication Data

US 2018/0249613 P1 Aug. 30, 2018

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
See application file for complete search history.

*Primary Examiner* — Keith O. Robinson
(74) *Attorney, Agent, or Firm* — Patrick J. Daugherty; Daugherty & Del Zoppo Co., LPA

(57) ABSTRACT

A new and distinct nectarine variety of *Prunus persica* named 'NJF20' is provided. This variety is distinguished from other nectarine varieties by its unique combination of medium sized non-showy flowers, fruit that are flat in shape, and firm melting, yellow, clingstone flesh that has very good eating quality for an early season nectarine due to its very sweet, low acid flavor.

6 Drawing Sheets

Latin name of genus and species of the plant claimed: *Prunus persica* L.
Variety denomination: 'NJF20'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of nectarine tree named 'NJF20'. The new tree resulted from crossing a proprietary nectarine seedling selection 'L5-225-01250' (non-patented) as the seed parent with a nectarine seedling selection 'Y153-69' (non-patented) as the pollen parent. The new variety differs from seed parent 'L5-225-01250' in that the new variety produces flat fruit with yellow flesh that are sweeter and ripen seven weeks earlier. In contrast, the seed parent 'L5-225-01250' produces round fruit with white flesh that tend to have a milder flavor. The new variety differs from pollen parent 'Y153-69' in that the new variety produces larger fruit that may be slightly more tolerant to bacterial leaf spot. The resulting tree was selected when growing in a cultivated area as the 23$^{rd}$ tree in the 13$^{th}$ row of Block H at a fruit research farm in Cream Ridge, N.J.

BRIEF SUMMARY OF THE INVENTION

The 'NJF20' variety is distinguished from other nectarine varieties due to the following unique combination of characteristics:

Produces early ripening, flat nectarines.

Fruit are medium-sized, glossy and well colored with a red-purple blush and a ground color that is an attractive yellow-orange.

Tree produces sweet, low acid, nectarine fruit of exceptional quality for the season.

Flesh of the fruit is yellow with a firm, melting texture.

'NJF20' differs from the related cultivar 'Flameprince' (unpatented), in that 'NJF20' fruit shape is oblate, has glabrous skin, and ripens very early, whereas 'Flameprince' fruit shape is round, has skin covered with hairs and ripens about 8 weeks later. 'NJF20' differs from the related cultivar 'White Lady' (U.S. Plant Pat. No. 5,821), in that 'NJF20' fruit shape is oblate, has glabrous skin, yellow flesh, and ripens very early, whereas 'White Lady' fruit shape is round, has skin covered with hairs, has white flesh and ripens about 4 weeks later.

Asexual reproduction of this new variety by budding onto 'Tennessee Natural VF 281.8' peach seedling rootstock (non-patented) shows that the foregoing characteristics are so reproduced.

The following detailed description concerns the original tree, 'NJF20'. The original tree has been observed growing in a cultivated area at the fruit research farm in Cream Ridge, N.J. Asexual progeny have been observed growing in cultivated areas at fruit research evaluation plantings in Elmer, N.J. and Bridgeton, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart* (1966)

BRIEF DESCRIPTION OF THE DRAWINGS

This new variety is illustrated by the accompanying photographic drawings, depicting the nectarine tree at three years of age by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
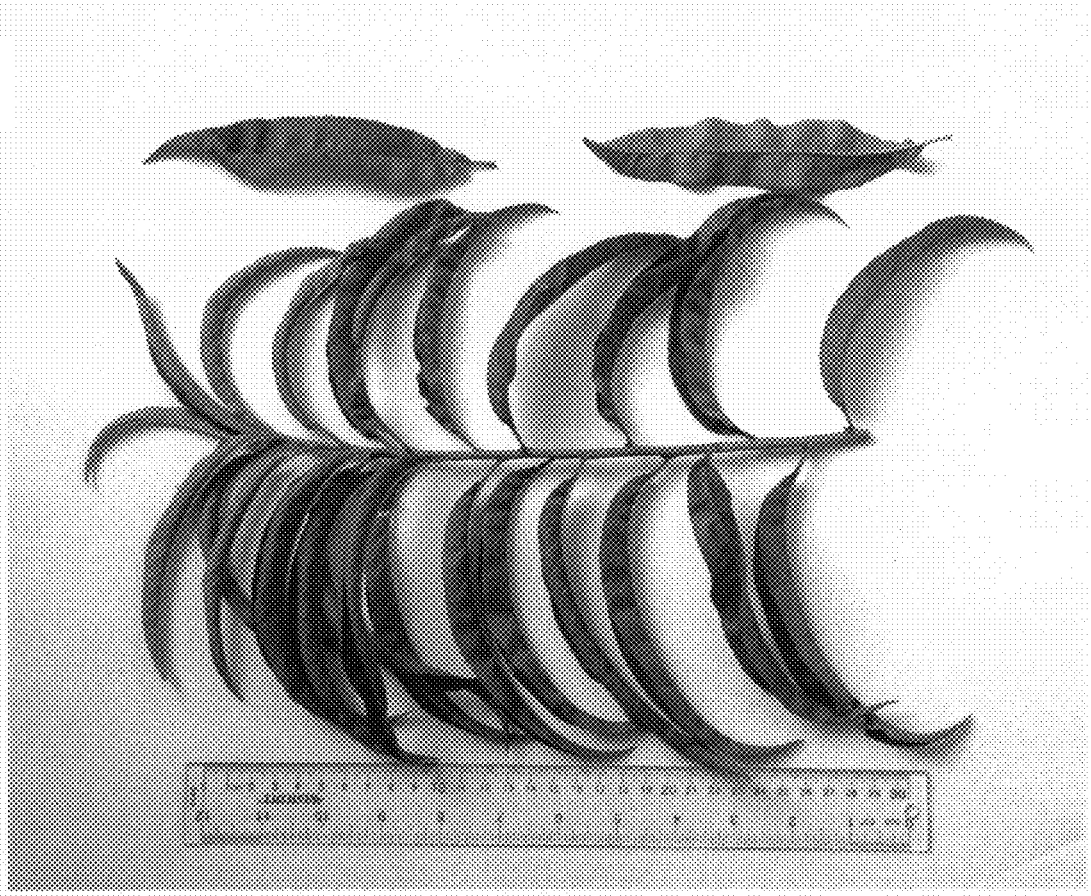
FIG. 1 is a color photograph taken on Sep. 9, 2016 of a characteristic twig of 'NJF20' in late summer bearing typical leaves of the foliage.
Figure 2:
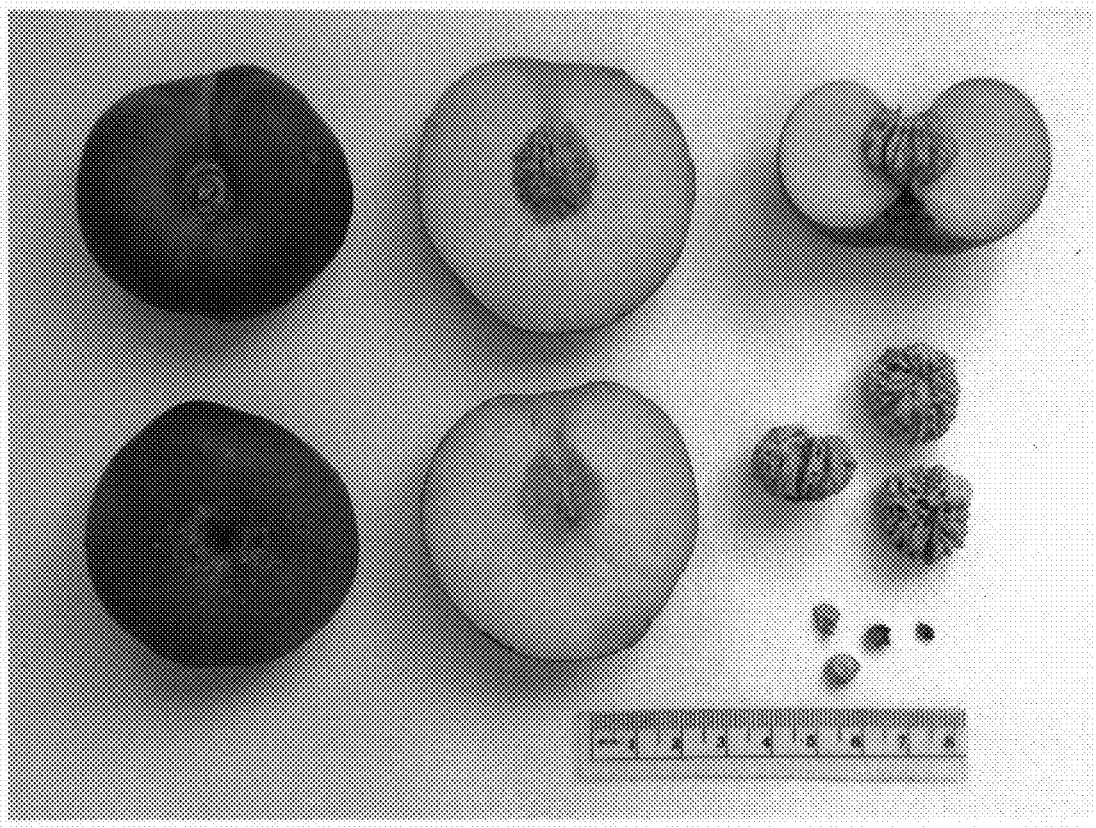
FIG. 2 is a color photograph taken on Jul. 12, 2016 of characteristic mature fruit, stones, and kernels removed from the stones, of 'NJF20'. Whole fruit are presented in three positions and both a transverse and longitudinal cross section to illustrate that the pericarp does not fully adhere to the pit when the fruit is mature. The stones exemplify the flat shape and mixture of single pits and rosettes of pits on the surface of the stone The kernels are of irregular form.
Figure 3:
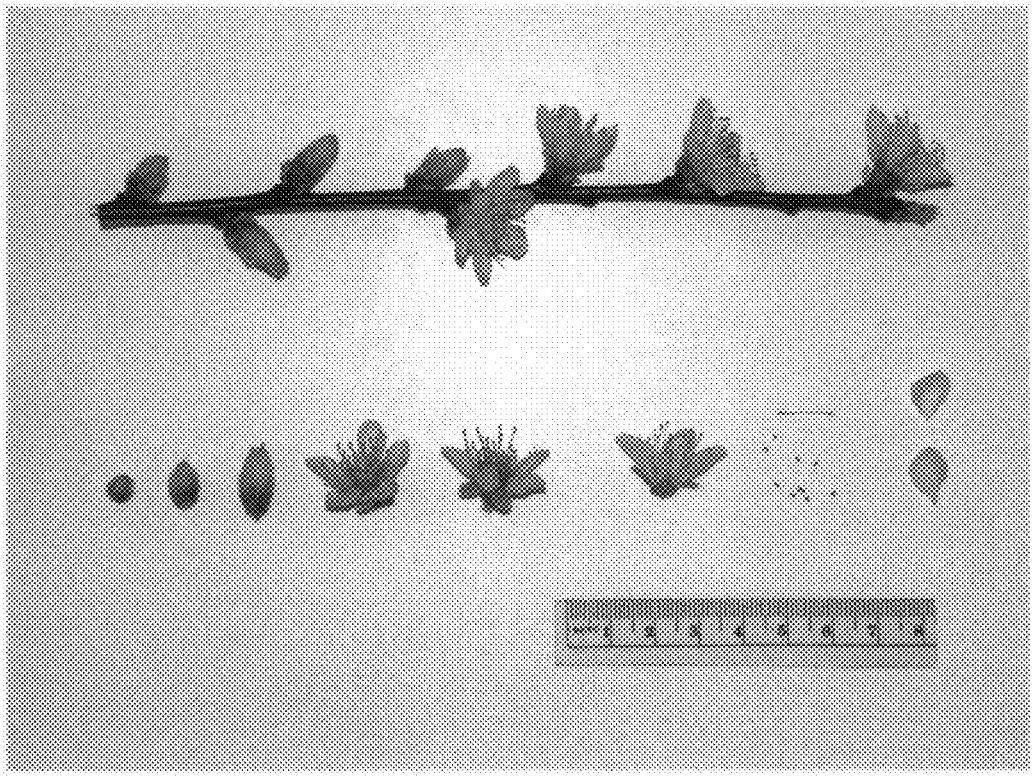
FIG. 3 is a color photograph of a characteristic twig that illustrates the typical flower buds and medium sized, non-showy flowers of 'NJF20', including a cross-section view of an open flower, and of petals and reproduction organ (pistil) removed from the flower, wherein the cupped, medium-sized, obovate-shaped petals have little to no undulation.
Figure 4:
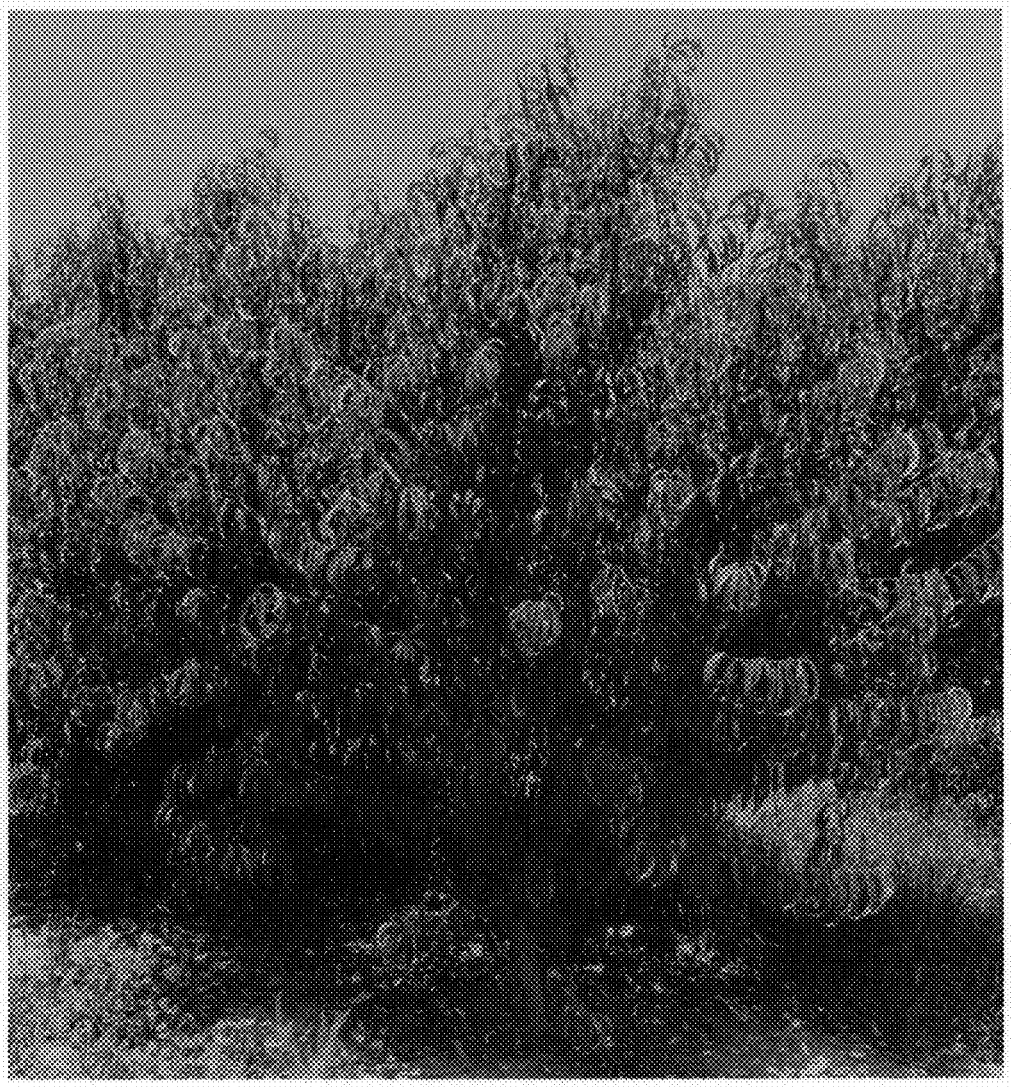
FIG. 4 is a color photograph of a tree of 'NJF20', during the summer, that illustrates the spreading growth habit of a tree at a fruit research evaluation planting in Elmer, N.J. on Jul. 27, 2016.
Figure 5:
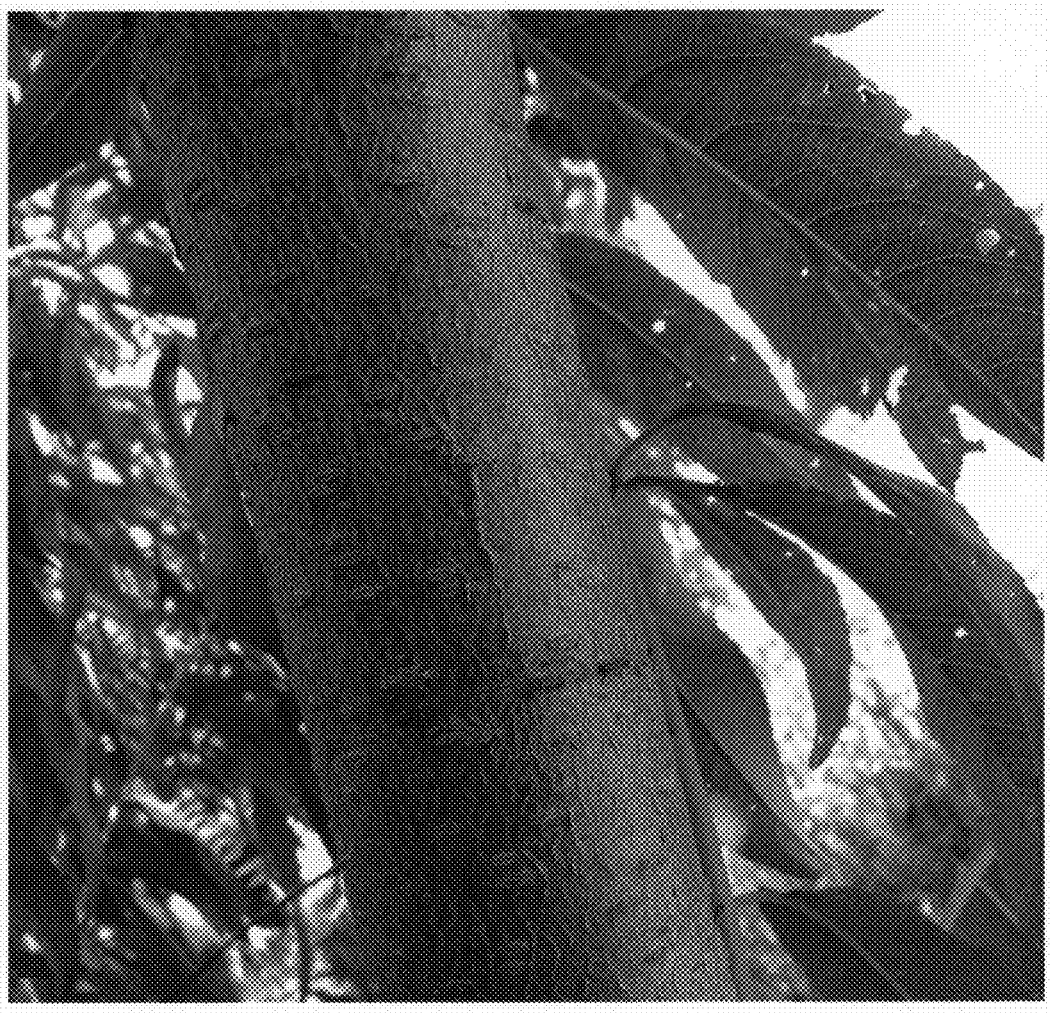
FIG. 5 is a color photograph taken on Jan. 25, 2017 of immature bark of 'NJF20' observed on a tree that illustrates color and low density of conspicuous elliptical lenticels on the immature bark.
Figure 6:
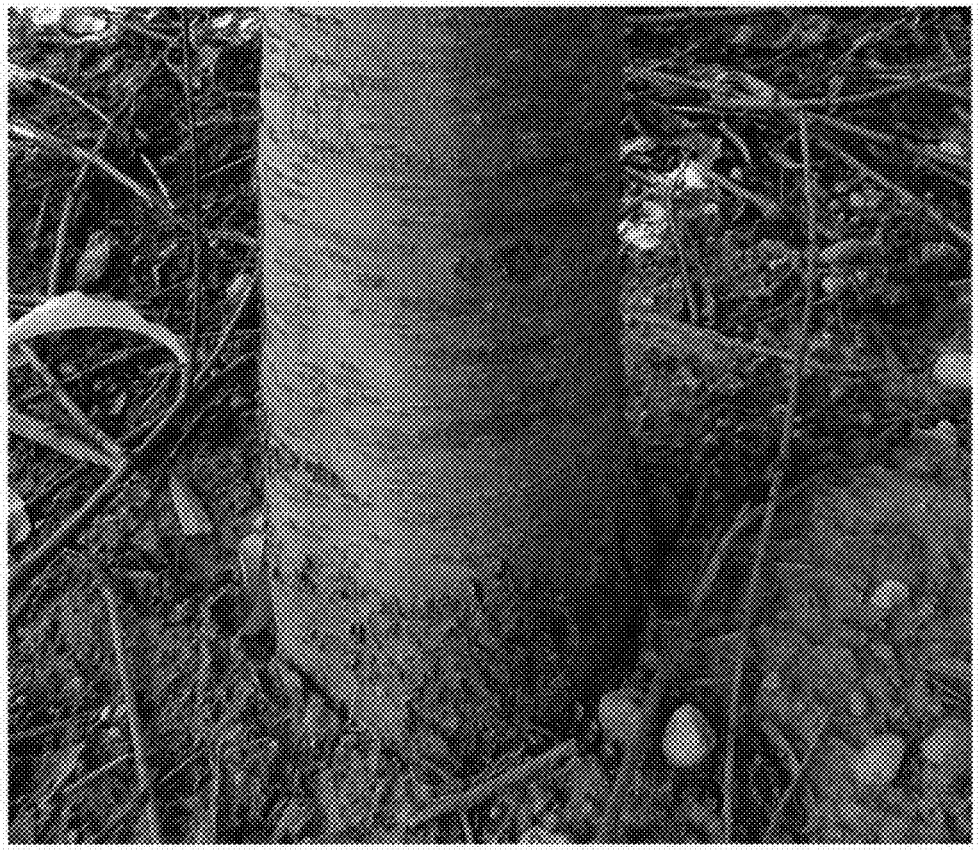
FIG. 6 is a color photograph taken on Jul. 27, 2016 of mature bark of 'NJF20' that illustrates the grey color, nearly smooth texture and prominent, large lenticels of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJF20' variety is based on observations of an asexually reproduced tree. The observed tree was three years of age and growing on 'Tennessee Natural VF 281.8' seedling rootstock (non-patented) at a fruit research evaluation planting in Elmer, N.J.

Scientific name: *Prunus persica* L.

Parentage:

*Seed parent*.—'L5-225-01250'.

*Pollen parent*.—'Y153-69'.

Tree:

*Vigor*.—Vigorous.

*Plant hardiness zone*.—Growth of plants has only been observed in zone 6b.

*Dormant flower bud cold tolerance*.—At least to −17° C.

*Overall shape*.—Spreading.

*Height*.—Average as compared to other nectarine cultivars. For example, measurement of a typical grafted tree on 'Tennessee Natural VF 281.8' peach seedling rootstock (non-patented) at three years after planting shows an average height of 3.4 meters when grown in Elmer, N.J.

*Width*.—Average as compared to other nectarine cultivars. For example, measurement of a typical grafted tree on 'Tennessee Natural VF 281.8' peach seedling rootstock (non-patented) at three years after planting shows an average width of 4.3 meters when grown in Elmer, N.J.

*Caliper*.—Three year old tree is 34 cm. in circumference measured at 20 cm. from the ground.

Trunk and branches:

*Trunk bark texture*.—Nearly smooth with prominent lenticels averaging 9.5 mm. in length and 2.4 mm. in width.

*Trunk bark color*.—Grey (between RHS 201C and RHS 201D).

*Primary branches*.—Branches that are approximately 15 cm. in circumference are greyed-orange (RHS 177D) overlaid with grey (RHS 201D).

*Lenticels*.—Low density, approximately 0.75 per square cm; elliptical in shape and conspicuous; typical examples of which averaged 5.0 mm. in length and 2.1 mm. in width.

*Lenticel color*.—Perimeter color is greyed-orange (RHS 164B) becoming greyed-orange (RHS 173D) towards the center.

*Branch pubescence*.—None.

*New growth bark*.—Anthocyanin coloration is present in the flowering shoot, generally greyed-purple (RHS 183B) in sun, becoming greyed-purple (RHS 187A) on well exposed shoot tips; greyed-purple (RHS 183B) over a yellow-green (between RHS 152C and RHS 152D) ground color in shade.

*Internodes*.—Length averaging 18.3 mm. on a one-year shoot.

Leaves:

*Texture*.—Glabrous, both surfaces.

*Sheen*.—Young leaves semi-glossy with a flat finish on the underside.

*Length*.—About 164 mm. to 202 mm., averaging about 181 mm. including the petiole.

*Width*.—About 29 mm. to 38 mm., averaging about 33.6 mm.

*Petiole*.—Averaging 10.6 mm. long and about 1.9 mm. in diameter.

*Margin*.—Crenate.

*Margin undulation*.—Slight, occasionally may have broad undulations.

*Form*.—Lanceolate, and concave in cross section.

*Apex*.—Sharply acuminate, typically sharply curved downward.

*Base*.—Acute.

*Venation*.—Pinnate.

*Glands*.—Number: About 3 to 6, averaging about 4.6. Position: Located on the leaf base and occasionally on the petiole. Size: Length averaging 1.2 mm. and width averaging 0.9 mm. Form: Reniform. Color: Yellow-green (RHS 151C).

*Stipules*.—None observed on mature leaves.

*Leaf color*.—Upper leaf surface: Yellow-green (RHS 147A). Lower leaf surface: Yellow-green (RHS 147B). Vein: Yellow-green (RHS 151D).

*Pubescence*.—None.

Flowers:

*Size*.—Non-showy, medium size, typical flower measuring between 23 mm. to 27 mm., averaging about 25 mm. across.

*Color*.—Dormant bud: Greyed-green (RHS 197C) becoming brown (RHS 200D) at base. Pink stage bud: Red-purple (between RHS 63A and RHS 63B). Open flower: Freshly opened flowers are red (between RHS 56B and RHS 56D) becoming red-purple (between RHS 63C and RHS 63D) at the petal's margins.

*Petals*.—Typically five petals per flower, cupped, medium sized, obovate, margin entire with little to no undulation, averaging about 12.1 mm. long and 9.0 mm. wide.

*Petal apex*.—Obtuse.

*Petal base*.—Cuneate at point of attachment.

*Stamens*.—Number: Variable, typical range 39 and 45, averaging 42.4. Length: Variable and generally shorter towards the center, between 9 mm. to 13 mm, averaging about 11 mm. Filament color: White (RHS 155A), becoming red-purple (RHS 63C) near petal fall. Anther color: Adaxial surface is red (RHS 53B); abaxial surface is yellow-orange (RHS 23D).

*Pistil*.—Number: One. Size: Length between 12 and 14 mm., averaging about 13.1 mm. Pistil color: Yellow-green (between RHS 145B and RHS 145C). Ovary: Small, medium length, glabrous, and flat in shape, color yellow-green (RHS 145A and RHS 145B). Stigma: located generally at the same level to slightly below the anthers.

*Sepals*.—Number: Five. Pubescence: about 0.4 mm long, high density. Color: Generally yellow-green (between RHS 148C and RHS 148D), sometimes overlaid with greyed-red (RHS 182B) near the base. Shape: Elliptic to ovate, with a flat base. Size: Length averaging 5.1 mm., width averaging 3.8 mm.

*Hypanthium color*.—Surface between the point of attachment of the petal/stamens and the ovary of the flower is Orange (between and RHS 25A and RHS 25B).

*Pollen*.—Abundant; yellow-orange (between and RHS 16A and RHS 16B) in color.

*Fragrance*.—None to very slight, sweet.

*Bloom season*.—Onset of bloom in Bridgeton, N.J. was on Apr. 15, 2015, with full boom on Apr. 19, 2015.

Fruit:

*Size*.—Medium for a flat nectarine, averaging about 3.5 cm. long, 6.3 cm. wide parallel to the suture and 6.5 cm. wide perpendicular to the suture.

*Typical weight*.—83 g.

*Form*.—Longitudinal section: Oblate. Traverse section: Triangular and slightly lipped.

*Suture*.—Generally shallow, extending from base to apex.

*Ventral surface*.—Nearly smooth to slightly depressed.

*Base*.—Depressed.

*Apex*.—Depressed; between nearly 5.7 mm. to about 8.4 mm. in diameter, with an average of 7.0 mm.

*Stem*.—Average length of 10.2 mm. and an average diameter of 7.8 mm.

*Skin*.—Thickness: Less than 1 mm. Surface: Glabrous. Tenacity: Medium. Astringency: None. Tendency to crack: Generally low, but medium to high if lightly cropped. Color: Blush is red-purple (between RHS 59A and RHS 59B); ground color is yellow-orange (between RHS 14B and RHS 14C) when present.

*Fruit properties*.—Flesh color: Yellow (RHS 13C), becoming yellow (RHS 13D) adjacent to stone. Glossiness: strong when firm-ripe, becoming medium when soft-ripe. Flesh adhesion: Generally clingstone, but may become semi-clingstone when fully ripe. Flesh firmness: Firm. Lenticels: conspicuousness is weak when firm-ripe, becoming medium when soft-ripe. Juiciness: Higher when soft-ripe relative to firm-ripe. Texture: Melting. Fibers: Not noticeable. Ripens: Between June 30 and July 9 at Cream Ridge, N.J. Flavor: Sweet, low acidity. Soluble solids: 16.0%. Aroma: Sweet, fruity. Eating quality: Good to very good.

*Keeping quality*.—Medium. Has held its flavor and firmness for at least 7 days in cold storage at 1° C. to 2° C.

*Shipping quality*.—Good. No bruising or scaring disorders have been observed.

*Usage*.—Dessert.

*Market*.—Local and long distance.

*Productivity*.—Medium. Trees have produced a full crop in 2 out of 5 and at least a partial crop 3 out of 5 years in Cream Ridge, N.J.

Stone:

*Type*.—Clingstone.

*Form*.—Flat.

*Shape*.—Slightly oblate in lateral view.

*Base angle*.—Greater than 90° wide.

*Apex angle*.—Greater than 90° wide.

*Surface*.—Mixture of single pits and rosettes of pits.

*Ventral suture*.—Low and may be deeply grooved on both sides from base to apex.

*External color*.—Orange-white (between RHS 159A and RHS 159B).

*Cavity surface color*.—Orange-white (RHS 159B).

*Average stone dry weight*.—2.2 g.

*Average stone wall thickness*.—Varies between 7.2 mm. along the dorsal ridge to 2.3 mm. at the base.

*Size*.—Large in relation to the fruit length, and medium in relation to the fruit width; averages about 13.9 mm. long, 20.9 mm. wide parallel to the dorsal ridge, and 18.8 mm. wide perpendicular to the dorsal ridge.

*Tendency to split*.—Typically low when well cropped.

Kernel:

*Form*.—Irregular.

*Skin color*.—Greyed-orange (between RHS 164B and RHS 165C).

*Vein color*.—Greyed-orange (between RHS 164B and RHS 165C).

*Viability*.—No.

*Size*.—Highly variable, forms only rudimentary seeds.

Plant/fruit disease and pest resistance/susceptibility: No atypical resistances/susceptibilities have been noted under normal cultural practices. Tolerant to bacterial leaf spot caused by *Xanthomonas campestris* pv. *pruni*.

I claim:

1. A new and distinct variety of nectarine tree, substantially as herein shown and described.

* * * * *